United States Patent [19]

Kuhn et al.

[11] Patent Number: 5,298,425
[45] Date of Patent: Mar. 29, 1994

[54] DEVICE FOR THE POSITIONALLY CORRECT FEEDING OF TEST STRIPS TO AN ANALYSIS UNIT

[75] Inventors: Hans-Jürgen Kuhn; Horst Menzler, both of Bernried; Stephan Sattler, Peissenberg, all of Fed. Rep. of Germany

[73] Assignee: Boehringer Mannheim GmbH, Mannheim, Fed. Rep. of Germany

[21] Appl. No.: 15,373

[22] Filed: Feb. 9, 1993

[30] Foreign Application Priority Data

Feb. 13, 1992 [DE] Fed. Rep. of Germany ....... 4204245

[51] Int. Cl.$^5$ .................... G01N 35/00; B23Q 7/12; B65H 9/00
[52] U.S. Cl. ...................... 436/43; 198/399; 198/400; 221/167; 221/173; 422/63; 422/99
[58] Field of Search ......... 422/63, 58, 67, 99; 436/43; 198/399, 400; 221/167, 173

[56] References Cited

U.S. PATENT DOCUMENTS

| | | | |
|---|---|---|---|
| 2,843,254 | 7/1958 | Vaughan | 221/173 X |
| 2,965,263 | 12/1960 | Haidegger | 221/162 |
| 3,035,681 | 5/1962 | Bennett | 198/399 |
| 3,139,172 | 6/1964 | McClelland et al. | 198/399 |
| 4,465,176 | 8/1984 | Long, Jr. | 198/400 |
| 4,777,907 | 10/1988 | Sanger | 198/399 X |
| 4,796,744 | 1/1989 | Sanger | 198/397 |
| 4,876,204 | 10/1989 | Inoue et al. | 436/46 |
| 4,972,935 | 11/1990 | Gross et al. | 198/395 |
| 5,097,938 | 3/1992 | Gruner et al. | 198/397 |

FOREIGN PATENT DOCUMENTS

0255675 2/1988 European Pat. Off. .
0336126 10/1989 European Pat. Off. .
950173 10/1956 Fed. Rep. of Germany .

*Primary Examiner*—James C. Housel
*Assistant Examiner*—Robert Carpenter
*Attorney, Agent, or Firm*—Nikaido, Marmelstein, Murray & Oram

[57] ABSTRACT

Device for the positionally correct feeding of test strips to an analysis unit. The test strips 10 include a base layer and at least one raised test field fixed to one side of the base layer. The test strips are contained disordered with respect to their longitudinal axis rotation position in a storage container. A separation and position correcting device 1 serves to feed the test strips 10 individually one after the other in a defined position to the analysis unit. Simplicity of construction and reliable operation are achieved due to the fact that the separation and position correcting device 1 includes a position correcting stage 30 with two rolls, between which a narrow gap 35 exists. The rolls rotate so that the surface 31a of the first roll 31 moves in the region of the gap 35 from top to bottom, while the surface 32a of the second roll 32 moves from bottom to top. The first roll 31 includes peripheral raised webs 37 which are in alignment with test field-free regions of the test strips 10. The second roll 32 is provided with axially parallel running drivers 38. The width of the gap 35 in the region of the raised webs 37 is smaller than the thickness of the test strips including the test field.

11 Claims, 2 Drawing Sheets

DEVICE FOR THE POSITIONALLY CORRECT FEEDING OF TEST STRIPS TO AN ANALYSIS UNIT

The invention relates to a device for the positionally correct feeding of test strips to an analysis unit. The test strips have a base layer, which usually consists of a rigid plastics film, and at least one test field fixed to one side of the base layer and raised relative to the surface of the base layer. The test field usually consists of a carrier matrix impregnated with reagents (usually paper, fabric or a porous plastics material).

For the carrying out of an analysis, the sample fluid (urine, blood, blood serum or another body fluid) has to be applied to the test field or—in the case of a multiple test strip—to a plurality of test fields, then a particular reaction time allowed to elapse and finally a physically detectable change specific to the analysis evaluated on the test field in an evaluation station. The physically detectable change is usually a colour change, which is measured photometrically. Other analysis principles are also known, however, in particular electrochemical tests, in which the physically detectable signal is an electric current or an electric voltage.

Independently of details of the analytical principle it is essential that the test strips of the analysis unit are fed in a positionally correct manner, i.e. the test fields must, at least in the evaluation station for evaluating the physically detectable change, and usually also in a sample application station in which the sample is applied (preferably completely automatically), be located in a particular position.

In order to ensure this, test strips are in many cases packed in magazines (for example EP-A-0 180 792, FIG. 15) in which they are located in ordered form in a position identical for all the test strips. This requires however a considerable expense on the packing of the test strips. The automatic withdrawal from magazines in the unit creates particular problems and stockkeeping by the manufacturer becomes complicated, because in addition to the magazine packs conventional tubular packs for manual or semi-automatic test strip analysis also have to be stocked.

The invention is consequently directed specifically towards cases in which the usual tube-shaped test strip packs are to be used, in which the test strips are aligned in one direction (i.e. the rear or front end of the strips is located at the same end of the tubes for all the strips), but with which the surfaces of the test fields do not run parallel but in different spatial directions, i.e. the test strips are disordered in respect of their longitudinal axis rotation position. In the case of such units a storage container is provided, into which the test strips are discharged directly out of the tube-shaped packs, so that they are present disordered (at least) with respect to their longitudinal axis rotation position.

In order to feed the test strips therefrom individually and in a positionally correct manner to the analysis unit, it is necessary to separate them and then bring them into the correct longitudinal axis rotation position (usually so that the test fields are directed upwards). Test strip analysis apparatus exhibit for this purpose separation and position correcting devices, which are also called "sorters".

In the development of sorters for test strips, particular problems result from the properties of the test strips. They are very light, usually not completely flat and on the whole highly flexible. The raised structures of the test fields, the materials used for the latter and the sharp edges of the base layer result in test strips easily getting entangled with one another. In addition, the test fields are very sensitive to mechanical contact.

In EP-A-0 180 792, EP-A-0 255 077 and DE-A-38 07 565 sorters are described with which the individual test strips are after the separation fed through a narrow shaft, it being possible for them to assume only one of two possible longitudinal axis rotation positions (e.g. "test field top" or "test field bottom"). Which of said two positions is adopted by the respective test strip is detected optoelectronically. On the further transport path of the test strips there is located a turning arrangement, which rotates the test strip through 180° about its longitudinal axis if necessary. The turning arrangement is activated if the optoelectronic detector indicates a "wrong" position. If the position of the test strip is correct, on the other hand, the turning arrangement is not activated. Behind the turning arrangement the test strips are all located in the same rotation position with respect to their longitudinal axis ("test field top"). From there they are conveyed by various means to the sample application station and to the evaluation station of the respective analysis unit.

This previously known principle requires a feeding to the narrow shaft, an optoelectronic detector and a rapid and reliably functioning turning mechanism. It is therefore expensive in constructional terms. The required reliability is at the same time not achieved in all cases.

It is therefore an object of the invention to create a device for the positionally correct feeding of test strips which is simple to construct, cost-effective and reliable in operation.

This object is achieved in the case of a device described at the outset in that the separation and position correcting device includes a position correcting stage comprising two rolls which are so dimensioned and positioned that a narrow gap exists between them, the rolls rotate in the same direction at a speed such that the surface of the first roll moves in the region of the gap from top to bottom, while the surface of the second roll moves from bottom to top, the first roll comprises on its surface peripheral raised webs which are so arranged that they are in alignment with test field-free regions of the test strips, the second roll comprises drivers running parallel to its axis and the width of the gap is smaller in the region of the raised webs than the thickness of the test strip including the test field.

The test strips do not have to be fed to the position correcting device with high precision. It suffices if they fall approximately parallel to the gap into the funnel-shaped space between the rolls. If the test strips are turned with respect to their longitudinal axis rotation position in such a way that the raised webs of the first roll engage with the spaces between two test fields, a "correctly" lying test strip drops through between the rolls. A test strip arriving in the "wrong" longitudinal axis rotation position cannot pass through the gap between the rolls. It is gripped by the drivers of the second roll on its longitudinal edge and rotated, so that it passes into the correct position and can be conveyed further through the gap between the rolls.

According to the invention the rotation or non-rotation of the test strips therefore takes place exclusively by means of extremely simple mechanical means. Neither a precise feeding of the test strips to a narrow conveying channel nor an electronic detection device is required. The rotating arrangement is not only of inexpensive and sturdy design, but may also be operated simply and with high reliability because only two rolls have to be rotated at preferably the same speed in the same direction.

The invention will be explained in detail below by means of an exemplifying embodiment illustrated diagrammatically in the figures, where FIG. 1 shows a separation and position correcting device in a highly schematized side view;

Figure 1:
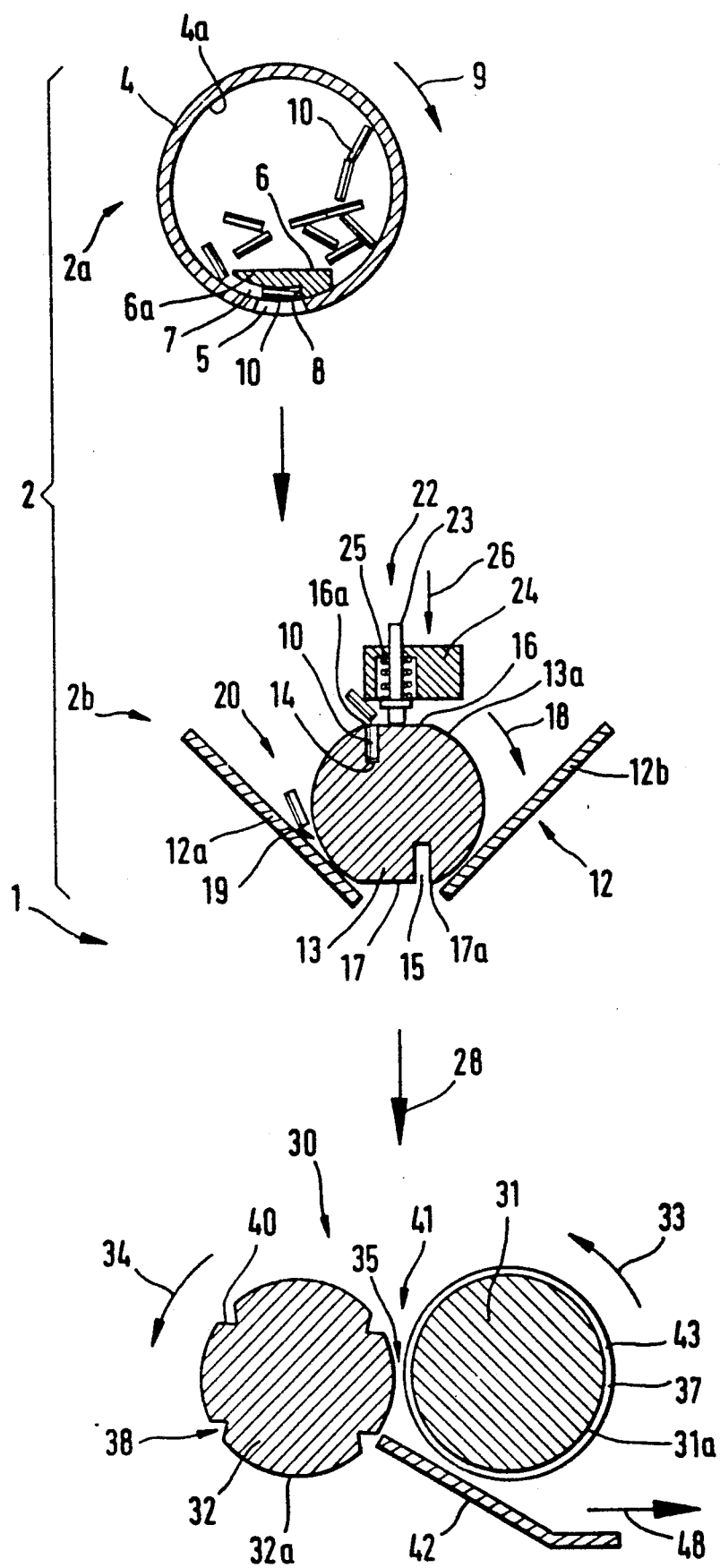

FIG. 1 shows a separation and position correcting device 1 for test strips, which consists of a separation stage 2 and a position correcting stage 30. The separation stage 2 is composed of two sub-stages 2a and 2b.

The first sub-stage 2a comprises a rotating drum 4 whose wall is provided in the axial direction with a slot 5 whose width is slightly greater than the width of a test strip 10. For the filling of the drum with test strips a sealable opening (not shown) is provided on the front side of the drum 4. Inside the drum 4 there is fixed a cam catch 6 which spans the slot 5 with a leg 6a running parallel to the inner wall 4a of the drum 4. A space 7 open to the front in the rotating direction is thereby formed. The leg 6a of the cam catch 6 extends in the rotating direction beyond the slot 5, the height of the space 7 corresponding roughly to the thickness of a test strip. The rear boundary, in the rotating direction, of the space 7 is formed by a stop face 8, which is in alignment with the rear edge, viewed in the rotating direction, of the slot 5.

The drum 4 is filled with test strips, which apart from their longitudinal axis rotation position have the same spatial alignment. If the drum 4 rotates in the rotating direction indicated by the arrow 9, the respective rotation causes a test strip 10 to be introduced into the space 7. The relative movement of the test strip 10 compared with the drum 4 is arrested by the stop face 8 of the cam catch 6. By virtue of the force of gravity the test strip 10 fall downwards through the slot 5 out of the drum. Because the height of the space 7 corresponds roughly to the thickness, and the width of the slot 5 corresponds roughly to the width, of the test strip 10, only one test strip 10 can pass through the slot 5 at a time.

In order to guarantee a reliable separation also in cases where the test strips 10 because of their particular properties get entangled with one another particularly easily, there is provided immediately after the first sub-stage 2a of the separation stage 2 a second sub-stage 2b.

The second sub-stage 2b comprises a funnel-shaped arrangement 12 which consists of two obliquely inclined surfaces 12a and 12b. A roll 13 is disposed in the centre of the funnel-shaped arrangement 12, each of the oblique surfaces 12a, 12b running tangentially to the roll 13. The roll 13 is provided with two receivers 14, 15 in the form of grooves of rectangular cross-sectional shape. There fits edge-wise into each of the receivers only one test strip 10, its longitudinal axis being aligned parallel to the axis of the roll 13. The depth of the receivers 14, 15 corresponds to the width of the test strips 10. In the region of the receivers 14, 15 the roll 13 is provided in each case with a flattening 16, 17 parallel to its longitudinal axis, the receivers 14, 15 being located in each case in the rotating direction of the roll 13 (arrow 18) in the vicinity of the rear edges 16a, 17a produced by the flattenings 16, 17. The oblique surface 12a running to the left of the axis of the roll 13 runs with a narrow gap 19 past the roll 13, the width of the gap being smaller than the thickness of a test strip 10 (including test field), so that no test strip 10 can slide through between the roll 13 and the oblique surface 12a.

The test strips 10 falling out of the first sub-stage 2a pass into a collection hopper 20 formed between the surface 12a and the roll 13, it being important that the collection hopper 20 is located on the side of the roll 13 in which its surface 13a moves from bottom to top. The falling movement of a test strip is arrested by the collection hopper 20. If one of the flattenings 16 or 17 of the roll 13 gets into the region of the gap 19, the latter increases in size, the test strip 10 slides further downwards and is received by one of the grooves 14, 15.

Above the roll 13 there is arranged a stripping device 22. A stripping element 23, which may be constructed as a circular pin or else as a ruler extending over the whole length of the roll, is supported in a vertical guide 24 in such a way that it is moveable radially to the axis of the roll 13. It is subjected to initial stress by means of a spring 25, so that it is pressed in the direction of the arrow 26 against the roll 13 and trails on the surface 13a of the roll 13. If one of the grooves 14, 15 moves through below the stripping element 23, as shown in the drawing, any additional test strip suspended on the test strip 10 located in the receiver 14 is stripped off and falls back into the collection hopper 20.

The oblique surface 12b on the right-hand side (i.e. on the side on which the surface 13a of the roll 13 moves from top to bottom) serves to prevent the test strips falling out of the receivers 14, 15 prematurely. Only when the respective bottom receiver 15 has reached approximately the vertical position shown in the figure does an individual test strip fall downwards out of the second sub-stage 2b and pass in the manner indicated by the arrow 28 into the position correcting stage 30.

The position correcting stage 30 forms the second stage of the separation and position correcting device 1. It comprises two cylinder-shaped rolls 31, 32 which rotate in the same direction (33, 34). The axes of the rolls 31, 32 run parallel to one another. Their spacing and the diameter of the rolls 31, 32 are coordinated with one another so that a narrow gap 35 exists rolls 31, 32.

The first roll 31 comprises peripheral webs 37. The second roll 32 is provided with axially parallel running drivers 38 which are formed as grooves 40 of triangular cross-section. The test strips 10 reach first of all the funnel-shaped space 41 existing between them, which passes over at its bottom end into the gap 35. Below the rolls 31, 32 there is arranged an oblique ramp 42 on which test strips 10 which have passed the position correcting stage 30 slide down in order to be fed to an analysis unit (not shown) (arrow 48).

Details of the position correcting stage 30 are shown in FIGS. 2 to 5.

The webs 37 are arranged peripherally on the surface 31a of the first roll 31 in such a way that their position, relative to the longitudinal direction of the test strip 10 in the gap 35, remains constant. In other words the webs 37 are projections from the cylinder surface 31a generated by rotation of a straight line around axis 31b which lie in each case in a plane running at right angles to the axis 31b of the roll 31. This condition must also be adhered to if instead of the cylinder-shaped rolls shown cone-shaped rolls are used, which is possible in principle, but less preferable.

An arrangement which is particularly simple to assemble and to manufacture is obtained if there are used for the formation of the webs shaped rings 43 of an elastic rubber material, for example O-rings, which sit in a corresponding groove 44 arranged peripherally on the surface 31a.

In the axial direction the webs 37 are attached to the roll 31 in such a way that they are in alignment in each case with one of the test field-free regions 10c of the test strips 10. In the preferred case shown the test strip 10 is a multiple test strip with a plurality of test fields 10b fixed one behind the other on a base layer 10a. In this case the roll should comprise at least three webs, at least one of which runs between two adjacent test fields, as is shown in FIG. 2 for the webs 37b and 37c.

It is naturally essential that the test strips 10 are fed with respect to their longitudinal position in such a way that their test field-free regions are in alignment with the webs 37a to 37d. This can take place in principle manually or by means of a handling mechanism (robot mechanism). If according to the embodiment shown in FIG. 1 the position correcting stage 30 is preceded by a separation stage 2, from which the test strips 10 fall freely into the funnel-shaped space 41, there is provided with expediency a longitudinal position guide 45, which in the case shown has a layout similar to that of a funnel, in which two oblique guide surfaces 46, 47 are disposed on the front ends of the rolls 31, 32 in such a way that a test strip 10 is guided into the correct position with respect to its longitudinal axis.

The dimensioning of the gap 35, the webs 37 and the drivers 38 is critical for the functioning of the position correcting stage. It can be determined empirically on the basis of the following explanations.

Figure 2:
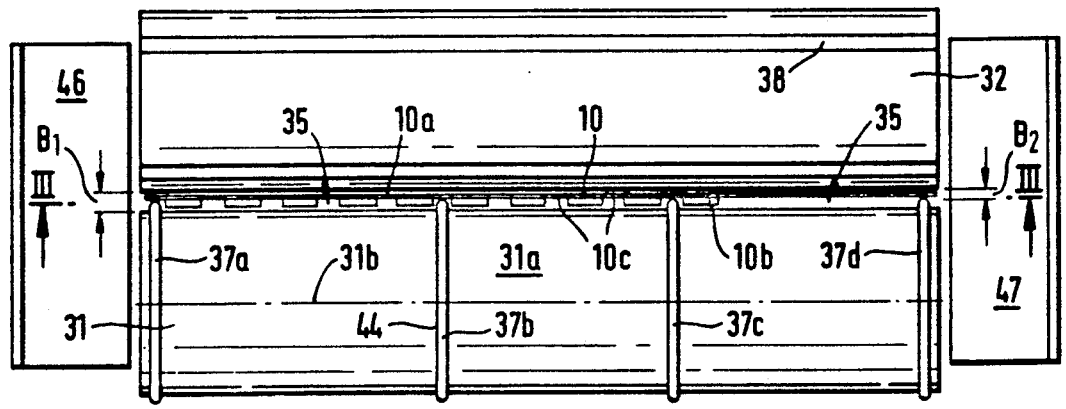
FIG. 2 shows a top view of a position correcting stage from FIG. 1.
Figure 3:
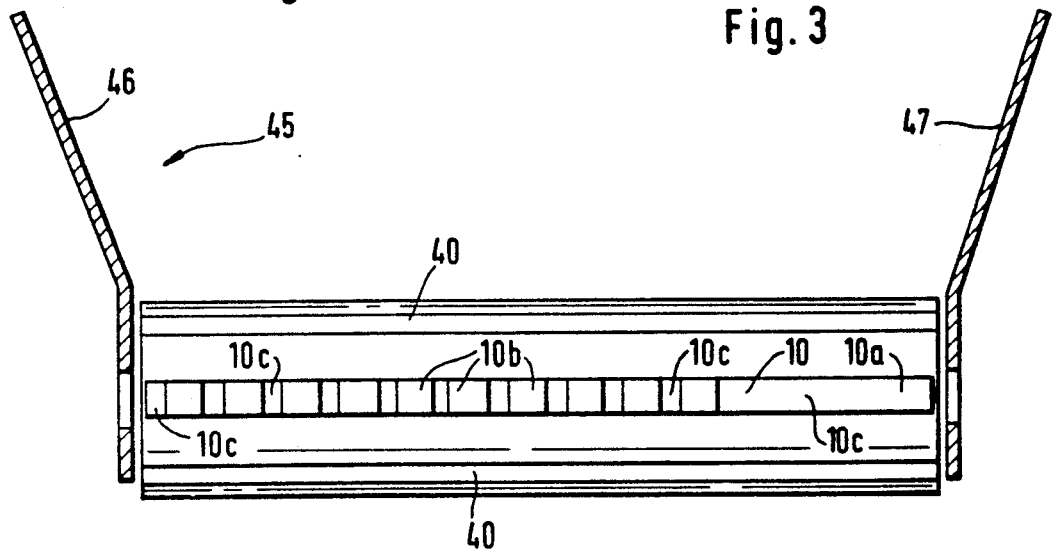
FIG. 3 shows a sectional view along the line III—III of the position correcting stage shown in FIG. 2.

The width $B_1$ of the gap 35 must be greater in the region of the test fields 10b than the thickness of the test strip 10 including the test field, so that a test strip 10, which in the "correct" longitudinal axis rotation position shown in FIG. 2 enters into the gap 35, may be conveyed vertically to its longitudinal axis through the gap 35. In any case, however, in the region of the webs 37 the width $B_2$ of the gap 35 must be smaller than the thickness of the test strip 10 including the test field. If—as in the case of the preferred embodiment shown—the roll 31 apart from the webs 37 has a smooth, cylindrical surface 31a, it follows from the latter that the height by which the webs 37 project out of the surface 31a should be slightly greater than the thickness of the test fields 10b (or in the case of different test field thicknesses than the thickest test field).

Figure 5:
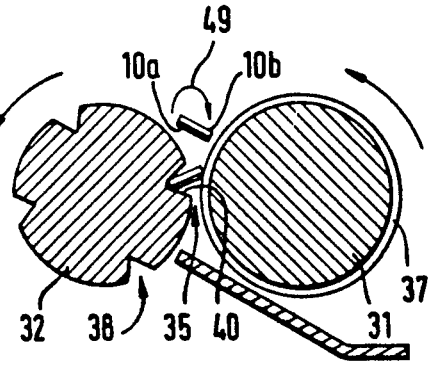

The rolls 31, 32 rotate, as mentioned, in the same direction, the roll 31 provided with the webs 37 rotating so that its surface 31a moves in the region of the gap 35 from top to bottom, while the surface 32a of the roll 32 moves in the region of the gap 35 from bottom to top. As a result of this rotation of the rolls and the dimensioning explained above, a test strip 10 which is so fed with respect to its longitudinal axis rotation position that its base layer is oriented towards the first roll 31 and its test fields 10b are oriented towards the second roll 32 ("wrong" longitudinal axis rotation position) is not conveyed through the gap 35. As FIG. 5 shows, one of the drivers 38 of the second roll 32 guides such a test strip 10 out of the gap 35 again. The drivers 38 are moreover formed in such a way that the test strip 10 receives simultaneously an impulse in the direction of a rotation about its longitudinal axis. The test strip 10 is thereby rotated in the manner indicated by the arrow 49 and brought into the "correct" position, in which the test fields 10b face towards the roll 31 and the base layer 10a towards the roll 32.

In order to support said longitudinal axis rotation from the wrong into the correct position, it is preferable if the test strip, the moment it has entered into one of the grooves 40, comes to lie at the same time against the webs 37 of the roll 31. It is also advantageous if the grooves 40 have an approximately triangular cross-section. The aperture angle should be relatively obtuse-angled (i.e. come to at least approximately 70°). The oppositely directed movement of the two rolls 31, 32 moreover supports the rotation about the longitudinal axis. The depth of the grooves 40 should therefore be calculated for instance so that the distance between the deepest point of the groove 40 and the webs 37 (in the position of the greatest approximation of the groove 40 to the roll 31) is somewhat (approx. 10 to 50%) smaller than the width of the test strips 10. it is also particularly advantageous if the webs 37, as explained above, consist of an elastic rubber material.

Figure 4:
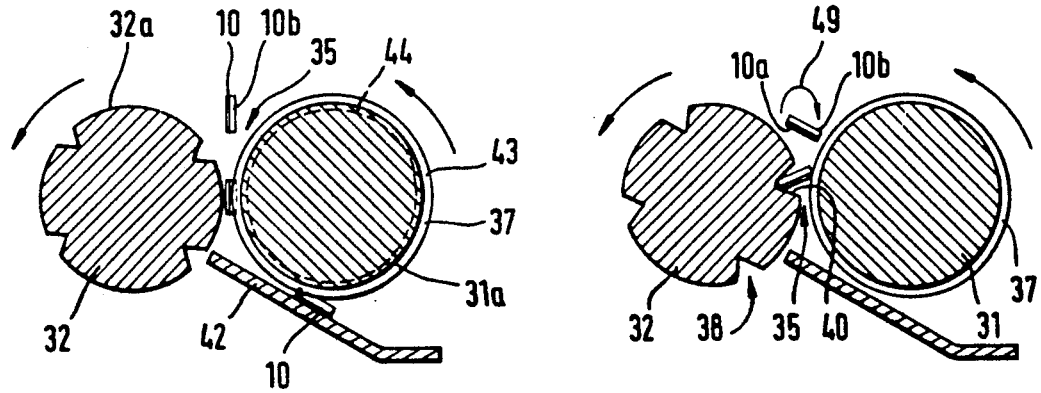
FIG. 4 and FIG. 5 show two views of the position correction stage of FIG. 1, which illustrate the operation of the latter.

As soon as a test, strip 10 is located in the correct position, it is conveyed through the gap 35 and is made ready by means of the ramp 42 for feeding to the analysis unit. If a test strip 10, as shown in FIG. 4, is fed in the correct position, it will be conveyed through the gap 35 without rotation.

We claim:

1. In an apparatus for the positionally correct feeding of test strips to an analysis unit, wherein said test strips include a base layer with at least one test field disposed on one side of the base layer and a plurality of regions on said one side of said base layer where no test field is present, said test field being raised with respect to the plurality of regions where no test field is present, said test strips being disordered with respect to their longitudinal axis rotation position in a storage container, said apparatus having a separation and position correcting device provided for feeding the test strips individually in a defined position to the analysis unit, the improvement wherein said separation and position correcting device comprises:

rotation position correcting means for correcting a rotation position of test strips with respect to the longitudinal axis thereof, said rotation position correcting mans having two rolls disposed adjacent each other with a gap therebetween, said rolls being disposed to rotate in a same direction of rotation wherein an outer peripheral surface of a first of said rolls adjacent said gap moves downward with respect to said gap, and an outer peripheral surface of a second of said rolls moves upward at said gap, said outer peripheral surfaces of said rolls forming a funnel shaped space above said gap, said space for receiving said test strips into said gap in an essentially parallel orientation of said gap and said test strips, wherein said first roll includes a plurality of peripheral raised webs on the outer peripheral surface thereof, said plurality of webs being disposed to be in alignment with at least a part of said regions of the test strips where no test field is present, and wherein said second roll is different form said first roll and includes a plurality of running driver portions, said running driver portions being parallel to said gap, wherein a width of the gap is reduced in a region of the plurality of raised webs such that a thickness of the test strips, including a test field, is greater than the width of the gap.

2. An apparatus for the positionally correct feeding of test strips as recited in claim 1, wherein the test strips are multiple test strips having a plurality of test fields disposed adjacent each other on the base layer with a test field free interstice between adjacent test fields, and wherein said first roll includes at least three peripheral raised webs, and at least one of said three webs is disposed in a test field free interstice of said test strips.

3. An apparatus for the positionally correct feeding of test strips as recited in claim 1, wherein said webs comprise rings of an elastic rubber material, and wherein said first roll comprises peripherally disposed grooves in a circumference thereof, and wherein said rings are positioned in said grooves.

4. An apparatus for the positionally correct feeding of test strips as recited in claim 1, wherein said plurality of running driver portions of said second roll comprise axial grooves in an otherwise smooth circumferential surface.

5. An apparatus for the positionally correct feeding of test strips as recited in claim 1, wherein said rotation positioning correcting means further comprises:

a longitudinal position guide for longitudinally positioning the test strips, wherein said test strips are guided in a longitudinal direction such that said part of said plurality of regions of said test strips where no test field is present are in alignment with the webs of the first roll.

6. An apparatus for the positionally correct feeding of test strips as recited in claim 1, wherein said separation and position correcting means further comprises separation means for separating said test strips, said separation means comprising a rotating drum having a slot in an outer peripheral surface thereof, said slot being disposed parallel to an axis of said drum, said rotating drum including a cam means arranged therein, adjacent said slot on an inner surface of the drum for guiding the test strips into the slot, wherein the test strips are guided to individually exit the drum.

7. An apparatus for the positionally correct feeding of test strips as recited in claim 1, wherein said separation and position correcting means includes separation means for separating said test strips, said separation means comprising a third roll which is a substantially rotationally symmetric rotating roll having parallel receivers therein, said parallel receivers for receiving individual test strips, said separation means further including stripping means for stripping a test strip which is entangled with one of said individual test strips disposed in one of said parallel receivers.

8. An apparatus for the positionally correct feeding of test strips as recited in claim 7, wherein said third roll includes a flattened portion on an outer surface thereof adjacent to each of said parallel receivers, and said separation and position correction means further comprises:

an obliquely inclined surface disposed adjacent to he third roll, with a distance between the third roll and the obliquely inclined surface such that the distance therebetween, at a smallest point thereof, is smaller than a thickness of a test strip including a test field.

9. An apparatus for the positionally correct feeding of test strips as recited in claim 1, wherein the stripping means comprises a stripping member disposed adjacent said third roll, said stripping member being radially guided relative to a rotating axis of the roll, said stripping member engaging the surface of the roll to strip a test strip which is entangled with the test strip located in one of said parallel receivers.

10. An apparatus for the positionally correct feeding of test strips as recited in claim 1, wherein the separation means further comprises a third roll, said third roll being substantially cylindrical and having parallel receivers disposed thereon, said parallel receivers for receiving individual test strips, said separation means including stripping means for stripping a test strip which is entangled with one of said individual test strips disposed in one of said axially parallel receivers.

11. An apparatus for the positionally correct feeding of test strips to an analysis unit, comprising the steps of:

providing a plurality of test strips which include a base layer and at least one test field disposed on one side of the base layer, said at least one test field being raised with respect to the one side of the base layer, said test strips being disordered with respect to their longitudinal axis rotation position in a storage container;

providing a separation and position correcting device for feeding the test strips individually in a defined position with respect to a longitudinal axis rotation position of the analysis unit;

providing a first roll having a plurality of peripheral raised webs on a surface thereof, said webs being disposed to be in alignment with regions of the test strips which are free of test fields, and also providing a second roll which is disposed adjacent to said first roll wherein said first and second rolls rotate next to each other with a gap therebetween, and wherein said second roll includes a plurality of running driver portions, said running driver portions being substantially parallel to said gap;

rotating said first roll and said second roll in a same direction of rotation wherein an outer peripheral surface of said first roll adjacent said gap moves downward with respect to said gap, and an outer peripheral surface of said second roll adjacent said gap moves upward; and feeding at least one of said plurality of test strips toward said gap, whereby said first and second rolls having said peripheral raised webs and said running driver portions, respectively, cooperate to correct a position of each of the test strips such that said test fields face the outer peripheral surface of said first roll.

* * * * *